United States Patent [19]

Winter, III

[11] 4,237,327

[45] Dec. 2, 1980

[54] PROCESS FOR HF-CATALYZED ALKYLATION OF AROMATIC HYDROCARBONS

[75] Inventor: George R. Winter, III, Mt. Prospect, Ill.

[73] Assignee: UOP Inc., Des Plaines, Ill.

[21] Appl. No.: 83,058

[22] Filed: Oct. 9, 1979

[51] Int. Cl.³ .............................................. C07C 2/66
[52] U.S. Cl. .................................... 585/450; 585/456; 585/464
[58] Field of Search ....................... 585/450, 456, 464

[56] References Cited

U.S. PATENT DOCUMENTS

| | | | |
|---|---|---|---|
| 3,275,702 | 9/1966 | Hutson | 585/456 |
| 3,413,373 | 11/1968 | Bloch | 585/450 |
| 3,426,092 | 2/1969 | Carson et al. | 585/302 |
| 3,484,498 | 12/1969 | Berg | 585/450 |
| 3,494,971 | 2/1970 | Fenske | 585/449 |
| 3,501,543 | 3/1970 | Hervert | 585/833 |
| 3,721,720 | 3/1973 | Chapmen et al. | 585/723 |
| 3,830,856 | 8/1974 | Anderson | 585/456 |
| 3,950,448 | 4/1976 | Witt | 585/449 |
| 4,072,730 | 2/1978 | Winter | 585/449 |

*Primary Examiner*—Curtis R. Davis
*Attorney, Agent, or Firm*—James R. Hoatson, Jr.; John F. Spears, Jr.; William H. Page, II

[57] ABSTRACT

A process for the HF-catalyzed alkylation of aromatic hydrocarbons is disclosed. A first overhead vapor stream removed from a first fractionation column which is used to regenerate the liquid-phase HF is passed directly into an upper intermediate point of a second fractionation column. A hydrocarbon stream containing the feed aromatic hydrocarbon and the product hydrocarbon is separated from liquid-phase HF and is then passed into the second fractionation column. HF dissolved in the hydrocarbon stream is removed from the second column as part of a second overhead vapor stream.

3 Claims, 1 Drawing Figure

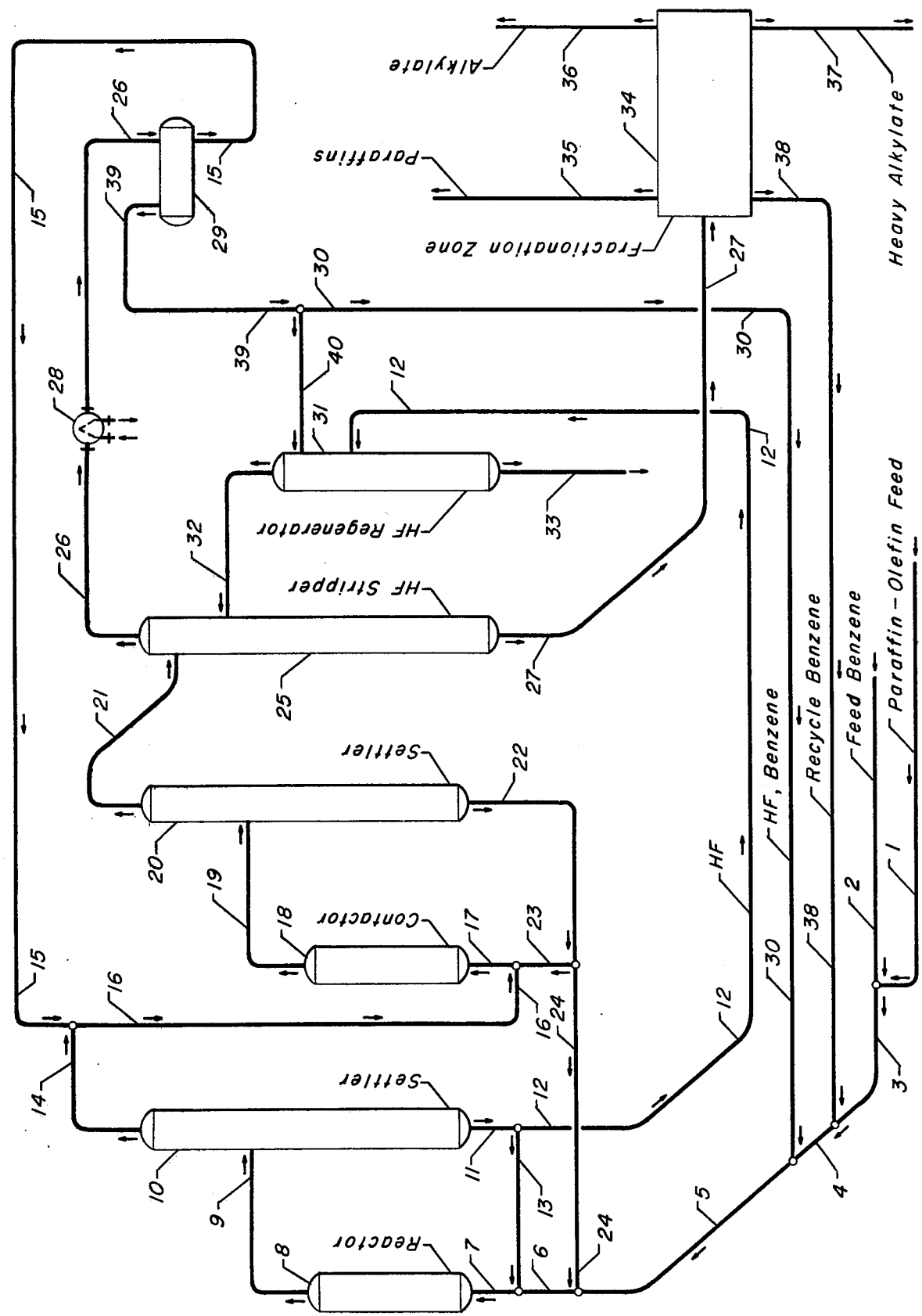

PROCESS FOR HF-CATALYZED ALKYLATION OF AROMATIC HYDROCARBONS

FIELD OF THE INVENTION

The invention relates to a hydrocarbon conversion process such as those often classified in Class 260. The invention more specifically relates to a process for the alkylation of aromatic carbon compounds by the introduction of an acyclic side chain using a catalyst comprising liquid-phase hydrogen fluoride. The invention is directly concerned with a process for the production of linear alkylbenzenes for use in detergent manufacture by the reaction of benzene with a $C_7$–$C_{20}$ monoolefin.

PRIOR ART

The alkylation of aromatic hydrocarbons using hydrogen fluoride as a catalyst is a well established art and is performed commercially on a large scale for the production of detergent grade alkylbenzenes. This process is commonly referred to as detergent alkylation. A representative example of the high state of the art is supplied by U.S. Pat. No. 3,950,448 (Cl. 260—671B). This reference describes the production of a soft detergent alkylate using a two reactor, two settling zone system similar in several respects to that preferred for use in the subject process. The reference also describes the regeneration of the HF used as catalyst and the purification of the products produced by the process. U.S. Pat. No. 3,494,971 (Cl. 260—671) presents another two reaction step detergent alkylation process. Other references directed to the production of detergent alkylate include U.S. Pat. Nos. 3,275,702 (Cl. 260—671); 3,426,092 (Cl. 260—671); 3,501,543 (Cl. 260—674); 3,501,544 (Cl. 260—674); 3,830,865 (Cl. 260—671R) and 3,484,498 (Cl. 260—671).

U.S. Pat. Nos. 3,721,720 (Cl. 260—683.48) and 3,975,164 (Cl. 23—288H) describe in some detail the separation of high boiling acid soluble oil from the HF used as catalyst in the production of motor fuel by the alkylation of isobutane with light olefins.

The passage of the overhead vapor stream of the HF regeneration column and the overhead vapor stream of the HF stripping column into a common single overhead condenser is practiced in the art.

BRIEF SUMMARY OF THE INVENTION

The invention provides an improved process for the HF-catalyzed alkylation of aromatic hydrocarbons. Both the capital and utilities cost of the process are improved. One broad embodiment of the invention may be broadly characterized as a process for the alkylation of aromatic hydrocarbons which comprises the steps of contacting a liquid phase mixture comprising an aromatic hydrocarbon, a normal paraffinic hydrocarbon and an aliphatic monoolefinic hydrocarbon within a reaction zone maintained at alkylation promoting conditions; passing the effluent stream of the reaction zone into a first settling zone and separating the first effluent stream into a first hydrocarbon stream comprising both the aromatic hydrocarbon and an alkylaromatic hydrocarbon and a first liquid phase HF stream; passing a portion of the first liquid phase HF stream into an HF regeneration zone comprising a first fractionation column from which there is removed a first overhead vapor stream comprising HF; contacting the first hydrocarbon stream with additional liquid phase HF in a contacting zone; separating the effluent stream of the contacting zone in a second settling zone into a second hydrocarbon stream comprising both the aromatic hydrocarbon and the alkylaromatic hydrocarbon and also dissolved HF and a second liquid phase HF stream; passing the second hydrocarbon stream into a second fractionation column operated at conditions effective to separate the second hydrocarbon stream into a second overhead vapor stream comprising the aromatic hydrocarbon and HF and a bottoms stream comprising the alkylaromatic hydrocarbons; recovering the alkylaromatic hydrocarbon product from the bottom stream of the fractionation column; and passing the first overhead vapor stream into the second fractionation column at an upper intermediate point.

DESCRIPTION OF THE DRAWING

The Drawing illustrates the preferred embodiment of the invention. For clarity and simplicity, various subsystems and apparatus normally required for the successful operation of the process have not been shown. These items include flow and pressure control valves, heat exchangers, pumps, control and monitoring systems, etc., which may be of customary design. This representation of the preferred embodiment is not intended to preclude from the scope of the invention those other embodiments set out herein or which are the result of reasonable and normal modification of the inventive concept by those skilled in the art.

Referring now to the Drawing, a feed stream comprising a mixture of paraffinic and olefinic hydrocarbons is passed into the process through line 1. This feed stream is admixed with a second feed stream entering the process through line 2 and which comprises high purity benzene. The resultant mixture of benzene, paraffins and olefins is passed through line 3 and admixed with a stream of recycled benzene carried by line 38. This new mixture is carried through line 4 to the junction with line 30 where it is admixed with a liquid phase stream of benzene which contains dissolved hydrofluoric acid (HF). To this newly formed admixture carried by line 5, there is added liquid phase HF from line 24 to form the liquid phase stream carried by line 6. An additional HF stream carried by line 13 is admixed with the stream carried by line 6 to form a stream comprising benzene, paraffinic hydrocarbons, olefinic hydrocarbons and liquid phase HF which is passed into the reactor 8 through line 7. It is also possible to pass the hydrocarbon stream flowing through line 5 directly into the reactor without prior admixture with the HF streams flowing through line 13 and 24. These HF streams would in this instance be passed into the reactor through a separate conduit.

The reactor 8 is maintained at alkylation promoting conditions to effect the reaction of the benzene with the olefinic hydrocarbons and to thereby produce an alkylaromatic hydrocarbon. This product alkylaromatic hydrocarbon is present in the effluent stream of the reactor which is carried by line 9. This effluent stream also contains benzene which is fed to the reactor in an amount in excess of that required by the reaction and the relatively inert paraffinic hydrocarbons. The reactor effluent stream also contains liquid phase HF. The effluent of the reactor is passed into a settling zone represented by the vertical settler 10. The conditions maintained within this settling zone allow the reactor effluent stream to separate into a less dense hydrocarbon phase and a more dense HF liquid phase. The more dense HF liquid phase is withdrawn through line 11 and divided into a first portion which is passed into the reactor through line 13 and a second portion which is passed into an HF regenerator through line 12.

The less dense hydrocarbon phase is removed at the upper end of the settling zone through line 14 and is admixed with a stream of regenerated HF carried by line 15. The thus-formed mixture of hydrocarbons and HF carried by line 16 is admixed with a stream of liquid phase HF carried by line 23 and is then passed through line 17 into a contactor 18 which is normally referred to in the art as a reactor. To avoid any possible ambiguity, zone 18 will be referred to herein as a contacting zone. It should be understood, however, that this zone is equivalent to those zones which are referred to as the second reaction zone in the previously cited references.

The effluent stream of the contacting zone is passed into a second settling zone 20 through line 19. The conditions maintained within the second settling zone allow the effluent of the contacting zone to separate into a less dense hydrocarbon phase removed through line 21 and a denser liquid phase HF stream removed through line 22. The liquid phase HF flowing through line 22 is internally recycled back to the reactor 8 and the contacting zone 18. The hydrocarbon stream removed from the top of the settler 20 through line 21 is passed into a fractionation column 25 referred to in the art as the HF stripper or HF stripping column. This fractionation column is so named because its function is to remove HF which is dissolved in the liquid phase hydrocarbons flowing through line 21. This produces a bottoms stream carried by line 27 which comprises the product alkylaromatic hydrocarbon, benzene and unreacted paraffins. This bottoms stream is passed into the fractionation zone 34. The fractionation zone will typically comprise three fractionation columns which separate the bottoms stream of the HF stripper into a stream of paraffinic hydrocarbons carried by line 35, which may be passed into a dehydrogenation zone, a stream of the product detergent alkylate carried by line 36, a relatively small stream of heavy alkylate carried by line 37, and a stream of recycle benzene carried by line 38.

The stream of liquid phase HF flowing through line 12 is passed into the fractionation column 31 utilized as an HF regenerator. This column may be reboiled by a means not shown to concentrate the relatively high boiling impurities present in the entering HF stream into a bottoms stream which is removed through line 33. This high boiling material is composed of a mixture of high bromine index compounds which, if allowed to enter the fractionation zone, would be concentrated into the product detergent alkylate thereby lowering the quality of the product. The overhead vapors present at the top of the stripping column are passed directly into the HF stripper 25 through line 32. The heat content present in the overhead vapors of the HF regenerator may therefore be utilized in the fractionation performed in the HF stripper. The overhead vapor stream of the HF stripper is removed through line 26 and passed through a total condenser 28. The resultant liquid stream is passed into a phase separator 29. The denser HF liquid is removed in line 15 as regenerated HF. The less dense hydrocarbon phase is rich in benzene and is removed in line 39 to be recycled to the reactor. A smaller first portion of this benzene stream is passed into the HF regenerator as reflux through a line 40, and a second portion is recycled to the reactor 8 through line 30.

DETAILED DESCRIPTION

One of the more important HF acid catalyzed alkylation reactions is the production of detergent grade alkylated aromatic hydrocarbons. This "detergent alkylate" is formed by the reaction of benzene with an olefinic hydrocarbon having from seven to twenty carbon atoms per molecule. A better quality detergent precursor normally results from the use of olefinic hydrocarbons having from about 10 to 15 carbon atoms per molecule.

The detergents produced from the resulting alkylated aromatic hydrocarbons are classified either as "soft" if they meet certain standards of biodegradability or as "hard" if they are relatively nonbiodegradable. Soft detergents are the result of using a long-chain monoolefin as the olefinic reactant. The preferred method of producing these olefins is by the dehydrogenation of the corresponding normal paraffins. The dehydrogenation zone may be integrated with the detergent alkylation process as described in U.S. Pat. Nos. 3,413,373; 3,484,498 and 3,494,971. Hard detergents result from the use of branched chain olefins such as propylene tetramer produced in a catalytic condensation process. The use of soft detergents is becoming more widespread, and the subject invention will therefore be discussed primarily in terms of soft detergent production.

It is the objective of this invention to provide a process for the HF-catalyzed production of alkylated aromatic hydrocarbons. It is a further objective to provide an improved process for the production of linear alkylbenzenes suitable for use in the production of detergents. It is a specific objective to reduce the capital and utilities cost of an HF-catalyzed process for the production of detergent alkylate.

The aromatic hydrocarbon which is alkylated in the subject process is preferably benzene, but may be a higher molecular weight aromatic hydrocarbon. The feed aromatic hydrocarbon may therefore be toluene, a xylene, ethylbenzene, phenol, naphthalene, etc. The olefinic hydrocarbon which is consumed in the production of detergent alkylate may have from about 6–20 carbon atoms per molecule. The preferred olefinic hydrocarbons are aliphatic monoolefins having from 10 to 15 carbon atoms per molecule. When these olefinic hydrocarbons are produced in a dehydrogenation process which is integrated with the alkylation process, it is common practice to pass the unseparated paraffin/olefin mixture produced as the effluent of dehydrogenation process into the alkylation process as the olefin-containing feed stream. This is basically because of the high cost of separating olefins and paraffins of the same carbon number. The olefin-containing feed stream charged to the alkylation process may therefore contain from about 30 to about 70 mol. % of straight chain paraffins having the same number of carbon atoms per molecule as the olefinic hydrocarbons. These relatively non-reactive paraffins pass through the alkylation process in the various hydrocarbon phase streams and are eventually separated from the alkylate by fractionation and then charged to the dehydrogenation process.

Chemical reactions which involve olefinic hydrocarbons and are catalyzed by hydrogen fluoride usually proceed at a very fast rate. To reduce the amount of olefin polymerization and to promote the production of a mono-alkylated aromatic product, the reactants are normally subjected to vigorous mixing and agitation at the point of initial contact of the olefinic hydrocarbons and the liquid-phase hydrogen fluoride. The desired result is a uniform dispersion and intimate contacting of the hydrocarbon and hydrogen fluoride phases and the avoidance of localized high temperatures or localized high concentrations of either the olefinic hydrocarbon or the hydrogen fluoride. The initial contacting of the reactants and the catalyst has been done in a number of different ways. For instance, the olefinic hydrocarbons have been sprayed into a mixture of hydrogen fluoride and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The reaction zone is maintained at alkylation-promoting conditions. As used herein, the term "alkylation-promoting conditions" is intended to include a pressure sufficient to maintain the reactants and HF in a liquid phase. A general range of operating pressures is from about 2 to 41 atmospheres absolute. The temperature range covered by this set of conditions is from about $-20°$ C. to about 95° C., but the reaction is preferably conducted at a temperature of from 15° C. to 50° C. The volumetric ratio of HF to the total amount of hydrocarbons entering the first reaction zone should be maintained within the broad range of from about 0.2:1.0 to about 10:1. A preferred range for this ratio is from 1.0:1.0 to 2.5:1.0. To lessen the production of polyalkylated benzenes and to reduce the amount of olefin polymerization in the first reaction zone, the mole ratio of benzene to the monoolefin at the point of initial olefin-acid contact is maintained above 1.0:1.0, but preferably below 10.0:1.0. A range of typical commercial ratios is from 3.0:1.0 to about 8.0:1.0.

The conditions maintained within the contacting zone, which is often referred to as the second reaction zone in most prior art references, are similar to these alkylation-promoting conditions, but some adjustment is required. For instance, since essentially all of the olefin has been consumed in the first reaction zone, the hydrocarbon stream fed to the contacting zone is substantially free of olefins. There is therefore no benzene to olefin ratio to be specified. The same pressure range may be used in the contacting zone as in the reaction zone, but a higher temperature is preferred. This higher temperature should be at least 6 to 10 centigrade degrees above that used in the reaction zone. All temperatures specified herein are intended to refer to the average temperature of the liquid stream entering the respective reaction zone.

The acid-catalyst ratio maintained in the contacting zone will normally be slightly lower, and a typical ratio is about 1.0:1.0. The purity of acid used in the contacting zone will, however, be higher. This is preferred because of the greater effectiveness of higher purity acid for the treatment of the alkylate. This treatment consists of the defluorination of the alkylate product and the extraction of naphthalenes and anthracenes. A higher acid purity is obtained by admixing the newly regenerated acid into the alkylate-containing hydrocarbon stream entering the contacting zone. The recycle acid for use in the reaction zone is withdrawn from the second settling zone and therefore contains a higher concentration of high molecular weight hydrocarbonaceous impurities. The acid used in the first and second reaction zones preferably contains about 85-92 wt. % HF and will typically be about 90 wt. % HF. The acid used in the contacting zone preferably contains more than 90 wt. % HF and is typically about 93-94 wt. % HF.

The effluent streams leaving the reaction zone and the contacting zone will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into settling zones.

The two settling zones will normally be maintained at a temperature which is set by the entering HF-hydrocarbon mixtures withdrawn from the respective upstream zones. They will therefore be at substantially the same temperature as the immediately upstream reaction or contacting zone. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 30 seconds but less than 30 minutes.

Those skilled in the art are familiar with the regeneration of the HF acid-catalysts. Information about the apparatus and conditions utilized for this operation is contained in the previously cited patents and also in U.S. Pat. No. 3,721,720. The regeneration operation is normally accomplished by stripping the acid under conditions sufficient to decompose alkylfluorides and to produce an overhead vapor stream containing HF and the stripping media. Benzene available within the process is a suitable stripping media. Heretofore, the overhead vapor stream of the column used to regenerate the HF was passed into a condenser. The resultant condensate was then allowed to separate into an acid phase and a benzene phase containing dissolved HF. The acid phase was withdrawn as the regenerated HF stream used in the contacting zone.

In the practice of the subject invention, the overhead vapor stream of the column used to regenerate the HF is passed directly into the HF stripping column. The overhead vapor stream is passed into the HF stripping column at an upper intermediate point. As used herein, the term "upper intermediate point" and similar terms is intended to indicate a point in the fractionation column which is separated from the top of the column by at least three fractionation trays but which is within the upper one-half of the column. The overhead vapor stream of the HF regeneration column will contain vapor-phase HF and the benzene or other aromatic hydrocarbon which is being alkylated. This vapor stream has a low concentration of the higher boiling impurities which it is desired to remove from the liquid phase HF stream fed to the HF regeneration column. The higher boiling materials are concentrated into a relatively small stream removed from the HF regeneration column as a net bottoms stream.

The aromatic hydrocarbon present in the overhead vapor stream of the HF regeneration column is derived mainly from the reflux liquid fed to the top of this column. A small amount of the aromatic hydrocarbon is also dissolved in the liquid phase HF stream fed to HF regeneration column. The reflux liquid may be derived from either of two potential sources. The reflux liquid may be removed from the HF stripping column at a point just below the location at which the overhead vapor stream of the HF regeneration column is passed into the HF stripping column. The reflux liquid is preferably removed from the overhead receiver which collects the condensed overhead of the HF stripping column. It is not necessary to supply reflux liquid for successful operation of the HF regeneration column if the feed stream is passed into the top of the column. However, the use of reflux is preferred since it increases the hydrocarbon content of the HF regeneration column's overhead vapor stream. This in turn lowers the optimum location for passage of the overhead vapor stream into the HF stripping column thereby increasing the length of the portion of the HF stripping column in which the heat content of the overhead vapor stream is utilized. The utilization of a liquid hydrocarbon stream instead of a liquid HF stream is believed to be novel.

The subject process is improved over the prior art in that the latent heat content of the overhead vapor stream of the HF regeneration stream is utilized within the process. This heat and some sensible heat aids in the fractionation performed in the upper portion of the HF stripping column. It is therefore not immediately rejected as low level heat in the overhead condenser. This reduces the utilities cost of operating the columns. In addition, only the overhead vapor stream of the HF stripping column needs to be condensed. This lowers both the required size and utilities cost of condensing the overhead vapor as compared to the prior art. The capital cost and the operating cost of the alkylation process are therefore reduced.

Representative conditions for the operation of the HF stripping column include an overhead vapor temperature of about 250° F. at a pressure of approximately 36 psig. There is normally no external reflux to this column. The overhead vapor stream of the HF stripping column is normally condensed by cooling it to about 100° F. or less. The HF regeneration column is operated at substantially the same pressure as the HF stripping column since they are in open communication. The bottoms liquid temperature required in the HF regeneration column will be above about 400° F.

The previously cited patents also describe fractionation systems and conditions suitable for use as an effective separation zone to recover the product alkylate from the bottoms stream of the HF stripping column. The bottoms stream of this HF stripping column is passed into a second fractionation column referred to as a benzene column. The benzene column is operated under conditions effective to cause the division of the entering hydrocarbons into a high purity benzene stream which is removed as the overhead liquid and a bottoms stream containing the alkylate product. This bottoms stream is passed into a third fractionation column referred to as a paraffin column. The non-reactive paraffins are removed as an overhead liquid stream. The bottoms stream of the third fractionation column comprises the product alkylate and any higher molecular weight hydrocarbons formed by side reactions. This bottoms stream is passed into a fourth fractionation column which produces a high purity overhead stream containing the detergent alkylate. A bottoms stream comprising polymerized olefins and polyalkylated benzenes (heavy alkylate) is removed for disposal. The third and the fourth fractionation columns are normally operated at a subatmospheric pressure. An alternative method of performing this separation is disclosed in U.S. Pat. No. 3,950,448.

In accordance with this description, one embodiment of the invention may be characterized as a process for the alkylation of aromatic hydrocarbons which comprises the steps of contacting a liquid-phase mixture comprising an aromatic hydrocarbon, a normal paraffinic hydrocarbon having from 7 to 20 carbon atoms per molecule and an aliphatic monoolefinic hydrocarbon having the same number of carbon atoms per molecule as the normal paraffinic hydrocarbon with liquid-phase HF within a reaction zone maintained at alkylation-promoting conditions; passing a first effluent stream, which is removed from the reaction zone, into a first settling zone maintained at quiescent conditions and separating the first effluent stream into a first hydrocarbon stream comprising the aromatic hydrocarbon and an alkylaromatic hydrocarbon and a first liquid-phase HF stream; passing a portion of the first liquid-phase HF stream into an HF regeneration zone comprising a first fractionation column wherein high-boiling impurities are concentrated into a first bottoms stream and from which there is removed a first overhead vapor stream comprising HF and the aromatic hydrocarbon; contacting the first hydrocarbon stream with liquid-phase HF in a contacting zone; passing a second effluent stream, which is removed from the contacting zone, into a second settling zone maintained at quiescent conditions, and separating the second effluent stream into a second hydrocarbon stream comprising the aromatic hydrocarbon, the alkylaromatic hydrocarbon and dissolved HF and a second liquid-phase HF stream; passing the second hydrocarbon stream into a second fractionation column operated at conditions effective to separate the second hydrocarbon stream into a second overhead vapor stream comprising the aromatic hydrocarbon and HF and a second bottoms stream comprising the alkylaromatic hydrocarbons; passing the second bottoms stream into a fractionation zone wherein the alkylaromatic hydrocarbon is recovered as a product; passing the first overhead vapor stream produced in the HF regeneration zone into the second fractionation column at an upper intermediate point; condensing the second overhead vapor stream to produce an overhead liquid which is separated into an HF phase which is passed into the contacting zone and a hydrocarbon phase; and passing a first portion of the hydrocarbon phase of the overhead liquid into the first fractionation column as reflux and passing a second portion of the hydrocarbon phase into the reaction zone.

I claim as my invention:

1. In a process for the production of linear alkylaromatic hydrocarbons which comprises the steps of:
   (a) contacting a liquid-phase feed stream comprising benzene and an aliphatic monoolefinic hydrocarbon having from 7 to 20 carbon atoms per molecule with liquid-phase HF within a reaction zone maintained at alkylation promoting conditions;
   (b) separating an effluent removed from the reaction zone in a first settling zone maintained at quiescent conditions into a first hydrocarbon stream comprising benzene and a linear alkylaromatic hydrocarbon and a first liquid-phase HF stream;
   (c) passing a portion of the first liquid-phase HF stream into an HF regeneration zone comprising a first fractionation column wherein high-boiling impurities are concentrated into a first bottoms stream and from which there is removed a first overhead vapor stream comprising HF and benzene;

(d) contacting the first hydrocarbon stream with liquid-phase HF in a contacting zone;

(e) separating an effluent removed from the contacting zone in a second settling zone maintained at quiescent conditions into a second hydrocarbon stream comprising benzene, the linear alkylaromatic hydrocarbon and dissolved HF and a second liquid-phase HF stream; and, (f) passing the second hydrocarbon stream into a second fractionation column operated at conditions effective to separate the second hydrocarbon stream into a second overhead vapor stream comprising benzene and HF and a second bottoms stream comprising the linear alkylaromatic hydrocarbon; the improvement which comprises passing the first overhead vapor stream produced in the HF regeneration zone into the second fractionation column at an upper intermediate point.

2. A process for the alkylation of aromatic hydrocarbons which comprises the steps of:

(a) contacting a liquid-phase mixture comprising an aromatic hydrocarbon, a normal paraffinic hydrocarbon having from 7 to 20 carbon atoms per molecule and an aliphatic monoolefinic hydrocarbon having the same number of carbon atoms per molecule as the normal paraffinic hydrocarbon with liquid-phase HF within a reaction zone maintained at alkylation-promoting conditions;

(b) passing a first effluent stream, which is removed from the reaction zone, into a first settling zone maintained at quiescent conditions and separating the first effluent stream into a first hydrocarbon stream comprising the aromatic hydrocarbon and an alkylaromatic hydrocarbon and a first liquid-phase HF stream;

(c) passing a portion of the first liquid-phase HF stream into an HF regeneration zone comprising a first fractionation column wherein high-boiling impurities are concentrated into a first bottoms stream and from which there is removed a first overhead vapor stream comprising HF and the aromatic hydrocarbon;

(d) contacting the first hydrocarbon stream with liquid-phase HF in a contacting zone;

(e) passing a second effluent stream, which is removed from the contacting zone, into a second settling zone maintained at quiescent conditions, and separating the second effluent stream into a second hydrocarbon stream comprising the aromatic hydrocarbons, the alkylaromatic hydrocarbon and dissolved HF and a second liquid-phase HF stream;

(f) passing the second hydrocarbon stream into a second fractionation column operated at conditions effective to separate the second hydrocarbon stream into a second overhead vapor stream comprising the aromatic hydrocarbon and HF and a second bottoms stream comprising the alkylaromatic hydrocarbon;

(g) passing the second bottoms stream into a fractionation zone wherein the alkylaromatic hydrocarbon is recovered as a product;

(h) passing the first overhead vapor stream produced in the HF regeneration zone into the second fractionation column at an upper intermediate point;

(i) condensing the second overhead vapor stream to produce an overhead liquid which is separated into an HF phase which is passed into the contacting zone and a hydrocarbon phase; and, (j) passing a first portion of said hydrocarbon phase of the overhead liquid into the first fractionation column as reflux and passing a second portion of said hydrocarbon phase into the reaction zone.

3. The process of claim 2 further characterized in that the aromatic hydrocarbon is benzene.

* * * * *